(12) United States Patent
Koizumi et al.

(10) Patent No.: US 8,477,183 B2
(45) Date of Patent: Jul. 2, 2013

(54) ENDOSCOPE SYSTEM AND LIGHT SOURCE DEVICE THEREFOR

(75) Inventors: Yugo Koizumi, Tokyo (JP); Susumu Kawata, Tokyo (JP); Takahiro Tanabe, Tokyo (JP); Toru Shinoda, Tokyo (JP); Akira Sambongi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/429,477

(22) Filed: Mar. 26, 2012

(65) Prior Publication Data

US 2012/0242812 A1 Sep. 27, 2012

Related U.S. Application Data

(63) Continuation of application No. PCT/JP2011/064533, filed on Jun. 24, 2011.

(30) Foreign Application Priority Data

Jul. 14, 2010 (JP) .................................. 2010-160117

(51) Int. Cl.
*H04N 7/18* (2006.01)

(52) U.S. Cl.
USPC .................................. 348/68; 348/65; 348/69

(58) Field of Classification Search
USPC ........................................................ 348/65–76
See application file for complete search history.

(56) References Cited

U.S. PATENT DOCUMENTS

| | | | | |
|---|---|---|---|---|
| 4,872,029 A | * | 10/1989 | Kato | ............................. 396/164 |
| 5,007,408 A | | 4/1991 | Ieoka | |
| 5,068,719 A | * | 11/1991 | Tsuji | ............................. 348/65 |
| 5,134,469 A | * | 7/1992 | Uchimura | ........................ 348/68 |
| 5,627,583 A | | 5/1997 | Nakamura et al. | |
| 5,868,666 A | | 2/1999 | Okada et al. | |
| 6,540,671 B1 | * | 4/2003 | Abe et al. | ....................... 600/180 |
| RE41,984 E | * | 12/2010 | Kitagawa | ......................... 348/79 |
| 2007/0123751 A1 | | 5/2007 | Takahashi | |
| 2007/0159526 A1 | * | 7/2007 | Abe | ................................ 348/65 |
| 2007/0225560 A1 | | 9/2007 | Avni et al. | |

FOREIGN PATENT DOCUMENTS

| | | |
|---|---|---|
| EP | 1 804 108 A1 | 7/2007 |
| JP | 60-232523 A | 11/1985 |
| JP | 64-76829 A | 3/1989 |
| JP | 03-021219 A | 1/1991 |
| JP | 05-277065 A | 10/1993 |
| JP | 07-171095 A | 7/1995 |
| JP | 09-164115 A | 6/1997 |
| JP | 2005-342147 A | 12/2005 |

OTHER PUBLICATIONS

Notice of Rejection Grounds dated Jun. 5, 2012 in related Japanese Patent Application No. 2012-520402.
European Search Report dated Mar. 7, 2013 from corresponding European Patent Application No. 11 80 6614.1.

* cited by examiner

*Primary Examiner* — Andy Rao
(74) *Attorney, Agent, or Firm* — Scully, Scott, Murphy & Presser, P.C.

(57) ABSTRACT

Under usual conditions, a first computation unit computes/outputs a first light adjustment signal in accordance with a photometric signal, and a second computation unit performs control of at least part of the endoscope system. The second computation unit computes/outputs the second light adjustment signal in accordance with the photometric signal together with the at least partial control while suppressing an increase in a processing load when an abnormality has occurred in the first computation unit.

8 Claims, 7 Drawing Sheets

ENDOSCOPE SYSTEM AND LIGHT SOURCE DEVICE THEREFOR

CROSS-REFERENCE TO RELATED APPLICATIONS

This application is based upon and claims the benefit of priority of the prior Japanese Patent Application No. 2010-160117, filed Jul. 14, 2010, the entire contents of which are incorporated herein by reference.

This is a Continuation Application of PCT Application No. PCT/JP2011/064533, filed Jun. 24, 2011, which was not published under PCT Article 21(2) in English.

FIELD

The present invention relates to an endoscope system.

BACKGROUND

An endoscope system includes, for example, a scope (endoscope) to be inserted into body cavities, a light source device and a video processor that are connected to that scope, a monitor device, and the like.

In body cavities, it is completely dark because there is no external light, and accordingly a light source device is necessary. A scope has, at its tip portion or the like, an image pickup device such as a CCD or the like and an outlet port for light (white light/RGB light or the like, which will be referred to as diagnosis light hereinbelow) provided by the light source device.

It has been necessary for alight source device to adjust an amount of light, for example because a necessary amount of light varies between direct observation and a picking up of images, because an appropriate amount of light varies in accordance with target sites, or because a necessary amount of light varies in accordance with distance between an observation target and the tip of the endoscope. For example, when the distance is small, a light amount is reduced so as to prevent blown-out highlighting from occurring in endoscopic images, and when the distance is great, a light amount is increased so that dark sites can be observed. This adjustment of a light amount is performed, for example, by switching between different lamps, varying electric power to be supplied to lamps, adjusting a diaphragm, or by using other means. This adjustment of a diaphragm is implemented according to the operation angle of diaphragm blades.

A conventional art and a background related to the above endoscope system are disclosed by, for example, Japanese Laid-open Patent Publication No. S60-232523.

Also, as disclosed by, for example, Japanese Laid-open Patent Publication No. H03-21219, the light source device of the above endoscope has conventionally used light of the colors of R (Red), G, (Green), and B (Blue), and etc. as illumination light (diagnosis light).

Also, as disclosed by Japanese Laid-open Patent Publication No. H03-21219 above, a frame sequential method and a color mosaic method (also referred to as a simultaneous method) are known as color image pickup methods for an electronic scope. As a frame sequential method, a method in which illumination light is switched to R (Red), G, (Green), and B (Blue) sequentially is known, as disclosed by, for example, Reference Document 1 (Japanese Laid-open Patent Publication No. S61-82731). As a color mosaic method, a method in which a filter array arranges, in a mosaic manner and on the front plane of the solid image pickup element, color transmission filters transmitting the colors R, G, B, and etc. is known, as disclosed by, for example, Reference Document 2 (Japanese Laid-open Patent Publication No. S60-76888). For a color mosaic method, the above diagnosis light is white light.

Also, as an example of a light source device of the above endoscope system, there is a configuration that includes a processor to control the entire light source device (referred to as a main CPU) and a processor dedicated to the function of adjusting a light amount (light adjustment function) (referred to as a computation dedicated CPU).

SUMMARY

The endoscope system according to the present invention is an endoscope system that includes an endoscope for emitting illumination light with which a subject is irradiated, comprising an illumination unit for emitting illumination light with which a subject is irradiated, an image pickup unit that is provided to the endoscope and that is for picking up an image of a subject illuminated by illumination light, a photometric signal generation unit for generating a photometric signal from the image pickup unit, a first computation unit for computing/outputting a first light adjustment signal in accordance with the photometric signal generation unit, a computation unit state detection unit for detecting a state of the first computation unit, a second computation unit that is for controlling at least part of the endoscope system, that is provided as a computation unit different from the first computation unit, and that computes/outputs a second light adjustment signal in accordance with the photometric signal generation unit together with the at least partial control while suppressing an increase in a processing load when the computation unit state detection unit has determined the first computation unit to be abnormal, a light adjustment signal control unit for outputting the first light adjustment signal computed/output by the first computation unit when the computation unit state detection unit has determined the first computation unit to be normal, and for outputting the second light adjustment signal based on the photometric signal generation unit by using the second computation unit when the computation unit state detection unit has determined the first computation unit to be abnormal, and a light adjustment unit for regulating the illumination light in accordance with the light adjustment signal output from the light adjustment signal control unit.

BRIEF DESCRIPTION OF DRAWINGS

The present invention will be more apparent from the following detailed description when the accompanying drawings are referenced.

DESCRIPTION OF EMBODIMENTS

Hereinafter, embodiments of the present invention will be explained by referring to the drawings.

Figure 1:
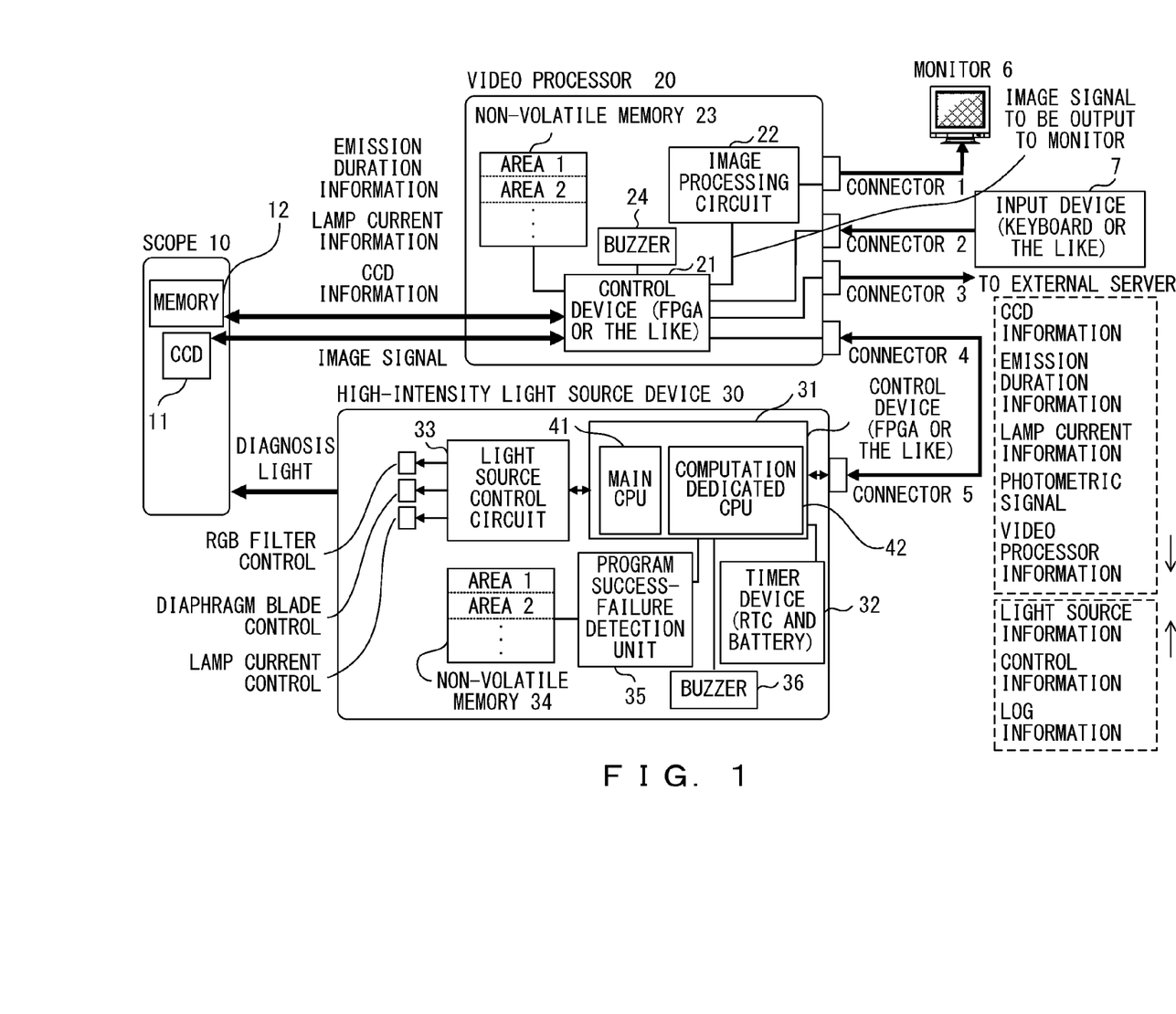
FIG. 1 shows an entire endoscope system according to a present embodiment.

FIG. 1 is an overall view of an endoscope system according to the present embodiment.

The endoscope system according to the present embodiment mainly includes a scope 10, a video processor 20, a high-intensity light source device 30, etc., and may further include a monitor 6, an input device (such as a keyboard or the like) 7, and the like. The video processor 20 and a high-intensity light source device 30 are connected to the scope (endoscope) 10. Although this connection configuration is a conventional configuration, and thus is omitted in the drawings, diagnosis light is output from the high-intensity light source device 30 to the scope 10, and image signals from the scope 10 are input to the video processor 20 as shown in the drawings. Also, the video processor 20 reads various types of information (which will be explained later in detail) from memory 12 in the scope 10.

The scope 10 is the main body of the endoscope to be inserted in a the body cavity of a patient, and includes a CCD 11, an outlet port (which is not shown, and is an outlet port to emit into a body cavity diagnosis light supplied from the high-intensity light source device 30), and the like similarly to conventional configurations. In other words, the scope 10 is an endoscope that emits illumination light (the above diagnosis light) with which arbitrary subjects in body cavities are irradiated. This endoscope includes an image pickup unit (CCD 11) to pick up images of subjects that are illuminated by illumination light.

The scope 10 according to the present embodiment incorporates the memory 12 (ROM or the like) that has beforehand stored various types of information (CCD information, emission duration information, lamp current information, and the like).

The video processor 20 includes a control device 21 such as an FPGA (Field Programmable Gate Array) or the like, an image processing circuit 22, non-volatile memory 23, a buzzer 24, and the like. The video processor 20 further has a plurality of connectors 1 through 4 as external interfaces. The connector 1 connects the system to the monitor 6, the connector 2 connects the system to the input device 7, the connector 3 connects the system to an external server (not shown), and the connector 4 connects the system to the high-intensity light source device 30.

As a matter of course, arbitrary communication cables are used for the connections between the connector 1 and the monitor 6, the connector 2 and the input device 7, the connector 3 and the external server, and the connector 4 and the high-intensity light source device 30, and arbitrary signals are transmitted and received through these communication cables.

Also, the above FPGA (Field Programmable Gate Array) is a type of gate array that allow users to write original logic circuits, and programmable logic devices that allow rewriting are sometimes defined as FPGAs.

The control device 21 inputs a pickup image signal (image signal) obtained by, for example, the CCD 11 of the above scope 10, and generates an "image signal for monitor output" from this image signal, and transfers the resultant signal to the image processing circuit 22. The control device 21 further generates a photometric signal on the basis of the input pickup image (image signal) obtained by the CCD 11, and this photometric signal is transferred to the light source device 30 via the connectors 4 and 5. This photometric signal is, in brief, a signal representing the luminance of a screen (images inside body cavities), and is used for controlling the light adjustment in the light source device 30.

In view of the above descriptions, it can be described that the control device 21 includes a photometric signal generation function (not shown) to generate a photometric signal on the basis of a pickup image obtained by the CCD 11.

The image processing circuit 22 displays on the monitor 6 images or the like of the body cavity of a patient in accordance with the above "image signal for monitor output". As a matter of course, the signal of this image is output to the monitor 6 via the connector 1.

The non-volatile memory 23 stores, for example, video processor information. Video processor information represents, for example, whether the method that is being employed is the frame sequential method or the simultaneous method.

In addition, as for the relationship between the scope 10 and the video processor 20, relating to the frame sequential method or the simultaneous method, the scope 10 always employs the same method as that employed by the video processor 20. Specifically, when the video processor 20 employs a frame sequential method, the scope 10 is compatible with the frame sequential method, while when the video processor 20 employs the simultaneous method, the scope 10 is compatible with the simultaneous method. Thereby, it can be described that the non-volatile memory 23 in the video processor 20 stores an illumination method (one of the frame sequential method and the simultaneous method) appropriate to its endoscope (scope 10).

In the initial process such as activation for example, the control device 21 reads various types of information (the above-described CCD information, emission duration information, lamp current information, or the like) stored in the memory 12 in the scope 10, and further reads the above video processor information from the non-volatile memory 23, and transfers to the high-intensity light source device 30 those various types of information that have been read. Thereby, it can also be described that the control device 21 has, as one of its processing functions, an illumination method reading function (not shown) to read the above illumination method (frame sequential method/simultaneous method) stored in the above non-volatile memory 23.

Also, the control device 21 generates the above-described photometric signal so as to transmit it to the high-intensity light source device 30 on an as-needed basis during the operation.

The high-intensity light source device 30 is provided with the shown connector 5, and the connector 4 and the connector 5 are connected to each other by an arbitrary communication cable so that communication between the high-intensity light source device 30 and the video processor 20 is performed through this communication cable. Accordingly, as a matter of course, the control device 21 uses this communication cable to transfer the above various types of information to the high-intensity light source device 30. The high-intensity light source device 30 and the video processor 20 transmit and receive data to each other through this communication cable so as to operate in a coordinated manner.

The high-intensity light source device 30 includes a control device 31 such as a FPGA, a timer device (RTC and a battery) 32, a light-source control circuit 33, non-volatile memory 34, a program success-failure detection unit 35, a buzzer 36, and the like. The high-intensity light source device 30 further includes, as an external interface, a connector 5 connected to the above communication cable.

The light-source control circuit 33 performs operations of RGB filter control, diaphragm blade control, and lamp current control in accordance with the control performed by the control device 31. The light-source control circuit 33 employs a conventional configuration such as that disclosed by Japanese Laid-open Patent Publication No. H03-21219 above, or the like, and thus detailed explanations thereof are omitted. The light-source control circuit 33 includes not only an electronic circuit, but also configurations to cause physical movements such as a motor, diaphragm blades, a rotation color filter, or the like. Brief explanations will be given of them below.

The light-source control circuit 33 includes a light-source lamp, a lamp control circuit, a motor, a motor control circuit, a diaphragm (diaphragm blades), a diaphragm control circuit, a rotation color filter, a motor movement control circuit, and the like disclosed by Japanese Laid-open Patent Publication No. H03-21219 above.

The rotation color filter includes color transmission filters of three colors, R, (Red), G (Green), and B (Blue), and thereby outputs the light of one of R (Red), G, (Green), and B (Blue) to the scope 10 as the diagnosis light (shown) so that the light is emitted from the tip of the scope 10 into the body cavity. By the above RGB filter control, the emission duration of each of R (Red), G (Green), and B (Blue) is controlled.

By the above diaphragm blade control, the angles of the diaphragm blades are adjusted and controlled by the diaphragm control circuit so that the amount of diagnosis light (the light intensity) is adjusted (diagnosis light is adjusted). By the above lamp current control, the amount of light emitted by the above light-source lamp is controlled by the above lamp control circuit so that the amount of diagnosis light is adjusted. By ordinary light adjustment control performed by a computation-dedicated CPU 42, light is adjusted by the coordination between the diaphragm blade control and the lamp current control.

The above control is performed in accordance with the above photometric signals, which is a conventional technique, and explanations thereof will be omitted.

Also, according to the configuration disclosed by Japanese Laid-open Patent Publication No. H03-21219, it is also possible to output white light from the light-source lamp directly to the scope 10 as the diagnosis light (shown) by moving the rotation color filter out of optical axis.

By utilizing this, white light is output to the scope 10 as diagnosis light when the connected video processor 20 (and the scope 10) employs the above "simultaneous method". When the connected video processor 20 (and the scope 10) employs the above "frame sequential method", the three colors of R (Red), G (Green), and B (Blue) are to be output sequentially by the above rotation color filter to the scope 10 as diagnosis light.

As described above, the high-intensity light source device 30 (the main CPU 41 for example) according to the present embodiment has a function of switching automatically to either the frame sequential method or simultaneous method (switching between illumination methods) in accordance with the type of the connected video processor 20 (and the scope 10). In other words, the high-intensity light source device 30 according to the present embodiment has a function of switching to either white light or RGB light as diagnosis light to be output to the scope 10. This performs automatic switching control between the frame sequential method and the simultaneous method in accordance with, for example, video processor information. Note that this function is referred to as an RGB filter switching control function or an illumination method switching function.

In addition, the initial processes are executed by, for example, the main CPU 41.

The timer device 32 includes an RTC (real-time clock) and a backup battery, and performs a timing operation. The non-volatile memory 34 stores arbitrary data (light source information, control information, log information, and the like).

The control device 31 transmits the above light source information, control information, log information, and the like to the video processor 20 at the time of the initial processes, such as the activation or the like or at a given point of time. Light information is data representing the current state of the light source (for example, whether the light is white light or RGB light) and control information and log information are, for example, various types of error information (information representing a lowered voltage of the battery, a failure in the computation-dedicated CPU, or the like), or the like.

The video processor 20 displays, for example, the above error information on the monitor 6, and reports the error to an external server (not shown) or the like.

The control device 31 includes the main CPU 41 and the computation-dedicated CPU 42. The computation-dedicated CPU 42 is a computation-dedicated CPU used exclusively for light adjustment. The computation-dedicated CPU 42 controls the light-source control circuit 33 in order to implement the automatic light adjustment function of the above scope 10. The computation-dedicated CPU 42 adjusts light in accordance with the coordination between the diaphragm blade control and the lamp current control.

The computation dedicated CPU 42 implements the automatic light adjustment function of the above scope 10 in accordance with the above various types of information (CCD information, lamp current information, and the like) read from the memory 12 and transferred to the high-intensity light source device 30 for the initial processes and also in accordance with the above photometric signal or the like that is transferred subsequently on an as-needed basis.

The lamp current information is information about the range (the upper limit value and the lower limit value) in accordance with the characteristics of the scope 10 (the CCD 11 of the scope 10). Accordingly, the light amount can be controlled to be within the appropriate range in accordance with the lamp current information. An appropriate light amount can be provided to its CCD 11 by obtaining lamp current information from the scope 10.

CCD information stored in the memory 12 represents appropriate luminance (light amount) in accordance with the type (characteristics) of the CCD 11 of the corresponding scope 10. The high-intensity light source device 30 decide the initial value of the light amount in accordance with CCD information. Thereafter, the light amount is adjusted and controlled in accordance with feedback information (photometric signals or the like).

When the video processor 20 (and the scope 10) employs the above frame sequential method, the above RGB filter control is also performed by the main CPU 41.

When the video processor 20 (and the scope 10) employs the above frame sequential method, the above emission duration information is also stored in the memory 12 of the scope 10, and this emission duration information is also transmitted to the high-intensity light source device 30 from the video processor 20. Thereby, the main CPU 41 executes RGB filter control in accordance with this emission duration information. This RGB filter control is capable of maintaining a stable luminance for each CCD by obtaining information about the opening duration (emission duration of each color of RGB) from the scope 10, and setting the obtained information, although the RGB filter control itself is based on a conventional technique, and is not explained accordingly.

The main CPU 41 is a central processing unit that controls the entire high-intensity light source device 30, and executes processes other than the light adjustment process performed by the computation dedicated CPU 42. For example, the main CPU 41 executes communication processes with the video processor 20, the above RGB filter control (only in the case of a frame sequential method), various flag checks (abnormality occurrence checks) that will be explained later, processes of controlling other configurations (not shown), and the like.

Also, the high-intensity light source device 30 is compatible with both the frame sequential method and the simultaneous method as described above, and has the above RGB filter switching control function so as to emit light by using either the frame sequential method or the simultaneous method. As described above, the frame sequential method and the simultaneous method are disclosed by, for example, Reference Documents 1 and 2 above, and the like.

In the initial processes at the activation, the control device 31 obtains the above various types of information by performing communications with the video processor 20 that is connected to the control device 31. The video processor information included in those various types of information represents the type (frame sequential method or simultaneous method) of the video processor 20, and the control device 31 switches to either the frame sequential method or the simultaneous method in accordance with this processor information. In other words, the control device 31 switches automatically the types (white light or RGB light) of light to be emitted in accordance with the type of the video processor 20 connected to the control device 31. However, this example is not limiting to the scope of the invention, and it is also possible for example to switch the types of light to be emitted in accordance with instructions from the video processor 20 (instructions from the user or the like).

Hereinbelow, explanations will be given for a case where the video processor 20 is a simultaneous method. The case of the frame sequential method, further performs RGB filter control, in addition to the case of the simultaneous method, and accordingly it can also be said that the explanations will also explain operations common for both the simultaneous method and the frame sequential method.

First, information (lamp current information and CCD information) necessary for light adjustment computation has already been stored in the memory 12 (ROM or the like) of the scope 10. This can also be interpreted as that lamp current information and CCD information are stored in such a manner that they correspond to each CCD.

As described above, information stored in the memory 12 is read by the video processor 20 in the initial processes and the like, and the read information is transferred to the high-intensity light source device 30, and thus the above current information and CCD information and the like are also transferred to the high-intensity light source device 30. Thereby, the high-intensity light source device 30 is capable of emitting an appropriate amount of light corresponding to the optical characteristics of the scope 10 (the CCD 11 of the scope 10).

Additionally, when a configuration without the memory 12 (ROM or the like) in the scope 10 is employed, the input device 7 (such as a keyboard) connected to the video processor 20 is operated by, for example, users so that the above lamp current information, the CCD information, and the like can be set arbitrarily. As a matter of course, the above lamp current information, the CCD information, and the like that have been set are transferred to the high-intensity light source device 30 from the video processor 20.

Hereinbelow, explanations will be given for a case where the video processor 20 has been determined to be the frame sequential method. In the case of the frame sequential method, approximately the same operations as those performed in the case of the above simultaneous method are performed, and operations related to RGB are also performed. Hereinbelow, explanations will be given for operations related to RGB.

In the case of the frame sequential method, the memory 12 (ROM or the like) of the scope 10 has beforehand stored the emission duration information of the color element of each color of RGB.

Because information stored in the memory 12 is read and transferred to the high-intensity light source device 30 by the video processor 20 in the initial processes or the like as described above, the above emission duration information of RGB is also transferred to the high-intensity light source device 30. Thereby, the high-intensity light source device 30 is capable of setting the emission duration/irradiation duration optimum to the optical characteristic of the scope (the CCD 11 of the scope 11).

Specifically, the emission duration/irradiation duration (emission duration/irradiation duration for the color element of each color of RGB) optimum to the optical characteristic of the CCD 11 of each scope 10 is arbitrarily set beforehand, and is stored in the memory 12 of the scope 10. Additionally, explanations for irradiation duration will be given as common explanations for emission duration/irradiation duration.

Light source devices have conventionally been provided with a configuration for controlling the irradiation duration of each color of RGB in accordance with set irradiation duration (the configuration disclosed by Japanese Laid-open Patent Publication No. H03-21219, for example). This conventional configuration will not be shown or explained in detail. However, brief explanations will be given for them. For an example, the main CPU 41 or the like sets, in the above conventional configuration, the irradiation duration of each color of RGB that has been read and transferred to the memory 12 of the scope 10 by the video processor 20. Thereby, the irradiation duration optimum for the optical characteristics of the scope 10 (the CCD 11 of the scope 10) that is being used currently can be set.

Although irradiation duration for each color element of RGB is stored in the memory 12 of the scope 10, this example is not limiting to the scope of the invention, and a non-irradiation duration may be stored for example. Non-irradiation duration means a time period other than the above irradiation duration in a prescribed cycle, and accordingly the main CPU 41 for example can obtain an irradiation duration from a non-irradiation duration. Alternatively, it is also possible to employ a configuration in which the irradiation duration of each color element of RGB is controlled in accordance with a non-irradiation duration that has been set. It is also possible to employ a configuration in which both irradiation duration and non-irradiation duration of each color element of RGB are stored in the memory 12 of the scope 10.

The above described example (an example in which data (irradiation duration and/or non-irradiation duration of each color element of RGB) stored in the memory 12 in the scope 10 beforehand is read and set) is not limiting to the scope of the invention. For example, the data (irradiation duration and/or non-irradiation duration of each color element of RGB) may be input and set arbitrarily from an external environment (for example, the input device 7 or the like).

In addition, hardware configurations and light adjustment control other than the above described aspects are the same as those performed in the case of a simultaneous method, and explanations thereof are omitted.

Figure 2:
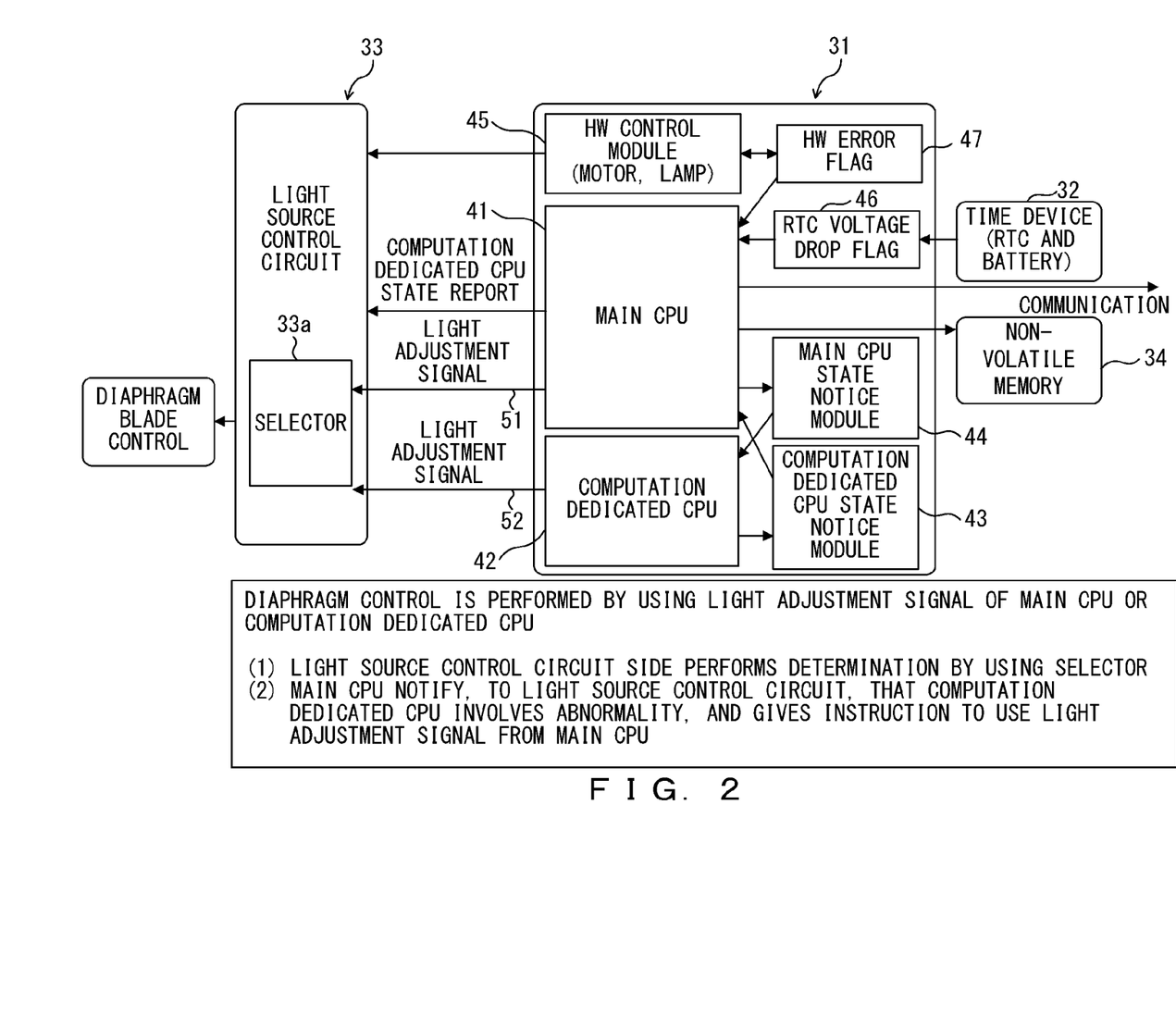
FIG. 2 shows a detailed configuration of a control device of a high-intensity light source device.

FIG. 2 shows a detailed configuration mainly of the control device 31 of the high-intensity light source device 30.

As shown in FIG. 2, the control device 31 of the high-intensity light source device 30 includes the main CPU 41 and the computation dedicated CPU 42 also shown in FIG. 1. Further, the control device 31 includes a computation dedicated CPU state notice module 43, a main CPU state notice module 44, an HW control module 45, an RTC voltage drop flag 46, and an HW error flag 47.

The computation dedicated CPU state notice module 43 detects a normality/abnormality of the computation dedicated CPU 42. The main CPU state notice module 44 detects a normality/abnormality of the main CPU 41. Both the computation dedicated CPU state notice module 43 and the main CPU state notice module 44 hold flags representing, for example, a normal state and an abnormal state, and reflect the detection results on the flags. For example, the flag is turned ON when an abnormality has been detected. The main CPU 41 and the computation dedicated CPU 42 determine whether the state is normal or abnormal by referring to these flags.

As described above, the computation dedicated CPU state notice module 43 substantially detects an abnormality in the computation dedicated CPU 42, and reports the detected abnormality to the main CPU 41. Similarly, the main CPU state notice module 44 substantially detects an abnormality in the main CPU 41, and reports the detected abnormality to the computation dedicated CPU 42.

The RTC voltage drop flag 46 is a flag indicating a voltage drop in the backup battery in the timer device 32. The timer device 32 has a function of detecting a voltage drop in a backup battery and a function of turning, to the ON state, the RTC voltage drop flag 46 when a voltage drop is detected in this backup battery. For example, the main CPU 41 can recognize a voltage drop of the backup battery by referring to the RTC voltage drop flag 46.

The HW error flag 47 is a flag indicating an error in the HW control module 45. The HW control module 45 has a function of detecting abnormalities in the HW control module 45 itself or other hardware (a motor, a lamp, or the like), a function of turning to the ON state the flag of the HW error flag 47 when an abnormality is detected, and other functions. For example, the main CPU 41 or the like can recognize the occurrence of an abnormality related to the HW control module 45.

When an error is detected in the HW control module 45, each of the modules and the CPUs 41 and 42 shift the high-intensity light source device 30 to a safe state. In the case of a motor failure, for example, because operations of the motor are dangerous, the high-intensity light source device 30 is shifted to a mode that prevents the motor from operating, or in the case of a lamp failure, the lamp is turned off. Note that there may be not only a single HW error flag 47, but may also be a plurality of HW error flags 47 that correspond to various failures (a motor failure, a lamp abnormality, and the like).

As described above, it is possible to perform error response processes after shifting the device into a safe state when an error has occurred by employing a configuration of detecting an error in the HW control module 45.

When a voltage drop of a backup battery is detected, the main CPU 41 or the like for example notify "voltage drop of backup battery" to the external server (not shown) via the video processor 20. Thereby, it is possible to expect beforehand that the timer operation of the RTC will halt so that the battery can be prevented from running out of power.

Also, when a flag is kept in an ON state until the device begins stable operations after the activation or the like, it is possible to prevent the device from performing unstable operations during the activation.

Note that the HW control module 45 employs a conventional configuration to control the motor, the lamp, and the like, and thus explanations thereof will be omitted. However, as shown in FIG. 2, control signals for the motor, the lamp, and the like are output from the HW control module 45 to the light-source control circuit 33, and the computation dedicated CPU 42 controls the HW control module 45 at least for the lamp current value so that the brightness of the lamp is controlled. Thereby, it can be said that the computation dedicated CPU 42 controls not only the diaphragm blades but also the lamp current value (the lamp brightness).

In this method, when an abnormality has occurred in the computation dedicated CPU 42, the main CPU 41 compensates for the light adjustment computation function so as to continue the automatic light adjustment function. However, because the main CPU 41 also controls the entire high-intensity light source device 30, very heavy processing loads are imposed on the main CPU 41 if the main CPU 41 continues the entire automatic light adjustment function that has been performed by the computation dedicated CPU 42. In some cases, processing loads on the main CPU 41 may become too large, causing an abnormality in operations of the main CPU 41.

In order to solve the above problems, the following first and second methods will be proposed herein. However, these methods are not limiting to the scope of the present invention.

In the first method, the main CPU 41 does not continue the entire automatic light adjustment function that has been performed by the computation dedicated CPU 42, but executes a "simplified automatic light adjustment function" (referred to as a simplified light adjustment function hereinafter). As specific implementations of this simplified light adjustment function, there are, for example, a method in which the lamp current control is halted so as to fix the lamp current value while only the diaphragm blade control is performed, a method in which the period of FB (feedback) control is extended, a method in which the gradation for the light adjustment is made coarse, and other methods. However, these examples are not limiting to the scope of the present invention, and an arbitrary simple computation algorithm may be executed in order to implement the simplified light adjustment function.

A method of extending the period of FB (feedback) control is implemented by shifting control for one frame to, for example, control for two or three frames. Specifically, while control for the screen of the endoscope is performed for each frame (for photometric signals of each frame) in conventional light adjustment control, in the present invention control is performed for each of two or three frames so that the control processing loads can be reduced. In other words, the main CPU 41 employs a computation cycle longer than that employed by the computation dedicated CPU 42 (i.e., a cycle for one frame in the above example) for the light adjustment.

Also, the above method in which the gradation of the adjusted light is made coarse is a method in which the step of controlling the diaphragm blades is made coarse (for example shifting from control in units of two degrees to control in units of five degrees or the like). In other words, the main CPU 41 employs an output range (in units of five degrees of the diaphragm blades in the above example) that is narrower than that employed by the computation dedicated CPU 42 (in units of two degrees of the diaphragm blades in the above example) for light adjustment.

In the second method, the main CPU 41 continues the entire automatic light adjustment function that has been executed by the computation dedicated CPU 42, and the control of the entire high-intensity light source device 30 is executed by a simplified algorithm (simplified as entire control hereinafter). In other words, the processing function originally to be performed by the main CPU 41 is limited so that the computation processing of the automatic light adjustment function is given priority.

In addition, the main CPU 41 may execute a recovery operation such as giving a reset signal to the computation dedicated CPU 42 parallelly to the execution of the process based on the first or the second method. Also, the main CPU 41 may store, as a log in the non-volatile memory 34, the fact that the computation dedicated CPU 42 was in an error state.

Figure 3:
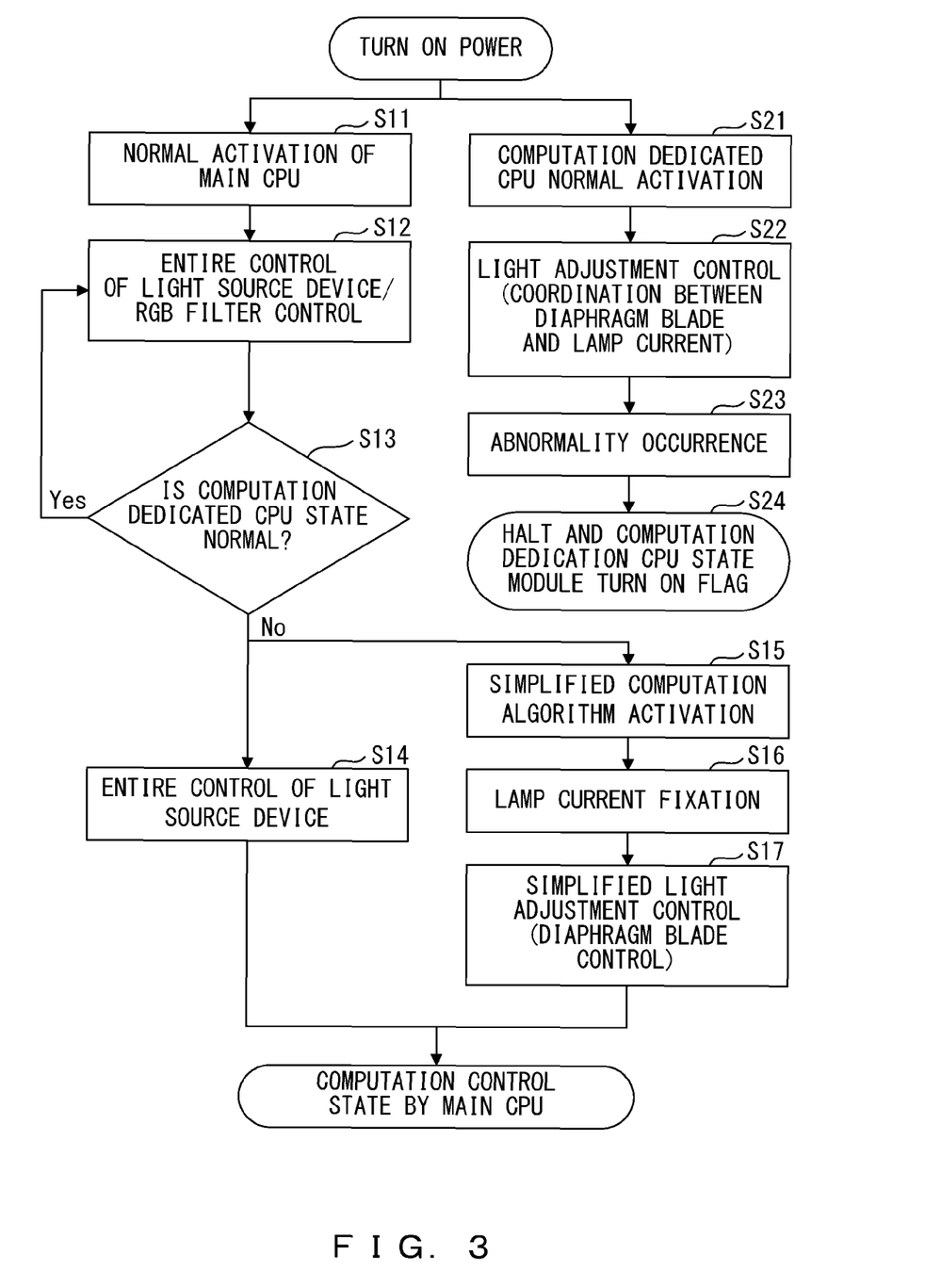
FIG. 3 is a flowchart explaining operations performed by the control device (first)

FIG. 3 shows a specific example of the first method.

FIG. 3 is a flowchart explaining operations performed by the control device 31 (first).

In FIG. 3, by turning ON the power source of the high-intensity light source device 30, the main CPU 41 and the computation dedicated CPU 42 execute prescribed activation processes (initial processes), respectively. In this example, these activation processes are assumed to be performed successfully (steps S11 and S21).

After the above normal activation, the main CPU 41 and the computation dedicated CPU 42 repeatedly execute prescribed processes, respectively. The main CPU 41 performs the control of the entire high-intensity light source device 30 as described above, and also performs RGB filter control in the case of the frame sequential method as described above (step S12). Also, the above entire control process includes, for example, a process of performing a periodic check about whether or not the computation dedicated CPU 42 is normal (step S13). In this check, the flag of the computation dedicated CPU state notice module 43 is referred to, and when the flag is ON, the situation is determined to be abnormal (NO in step S13), and when the flag is OFF, the situation is determined to be normal (YES in step S13). When the situation has been determined to be normal (YES in step S13), the process returns to step S12, and continues the above ordinary processes (various types of the entire control (including the RGB filter control in the case of the frame sequential method)).

Meanwhile, the computation dedicated CPU 42 is performing a computation process for the above described automatic light adjustment function (control of the coordination between the diaphragm blades and the lamp current) (step S22).

In addition, the main CPU 41 or the computation dedicated CPU 42 outputs an arbitrary control signal to the light-source control circuit 33 in order to implement the above RGB filter control, diaphragm blade control, and lamp current control.

When an abnormality has occurred in the computation dedicated CPU 42 at an arbitrary point in time (when a failure or the like has occurred) (step S23), the computation dedicated CPU 42 halts, and the computation dedicated CPU state notice module 43 detects this abnormality so as to turn ON the flag of the computation dedicated CPU state notice module 43 itself (step S24).

Thereby, when the main CPU 41 performs the process of step S13 thereafter, an abnormality is detected (NO in step S13), and the process proceeds to steps S14 through S17. In addition, it is also possible to say that if the processes of steps S12 and S13 are the process in the ordinary mode of the main CPU 41, the process of steps S14 through S17 are the process in the special mode of the main CPU 41. In other words, it is also possible to say that the main CPU 41 operates in the ordinary mode until a result of the step S13 becomes NO, and shifts to the special mode when the result of the step S13 has become NO.

The process in step S14 is approximately the same as that in step S12, and is constituted of various types of entire control (including the RGB filter control in the case of a frame sequential method). In other words, the various types of entire control, which are inherently to be performed by the main CPU 41, are continued after a failure of the computation dedicated CPU 42.

Processes in steps S15, S16, and S17 are executed parallelly to the process in step S14.

First, the above simplified computation algorithm for implementing the simplified light adjustment function described above is activated (step S15). Thereby, the simplified light adjustment function in steps S16 and S17 is realized. Specifically, the lamp current value is fixed (step S16), and only the diaphragm blade control is performed (step S17). As described above, by substantially bypassing the control related to the lamp current value, the processing loads on the main CPU 41 are reduced. Further, it is also possible to perform the control of extending the period of the above described FB (feedback) control or perform the control of making coarse the gradation of light adjustment in the diaphragm blade control in step S17. Thereby, the processing loads on the main CPU 41 are reduced further.

As a matter of course, the main CPU 41 receives processing loads heavier than those in the ordinary mode. However, it is possible to reduce an increase in processing loads.

Note that the above lamp current value (fixed value) is included, for example, in the program of the above simplified computation algorithm.

Also, only diaphragm blade control is performed while skipping lamp current control in the above example; however, this example is not limiting to the scope of the present invention, and it is also possible to perform only lamp current control while skipping diaphragm blade control (by fixing the angles of the diaphragm blades or by other means).

Figure 4:
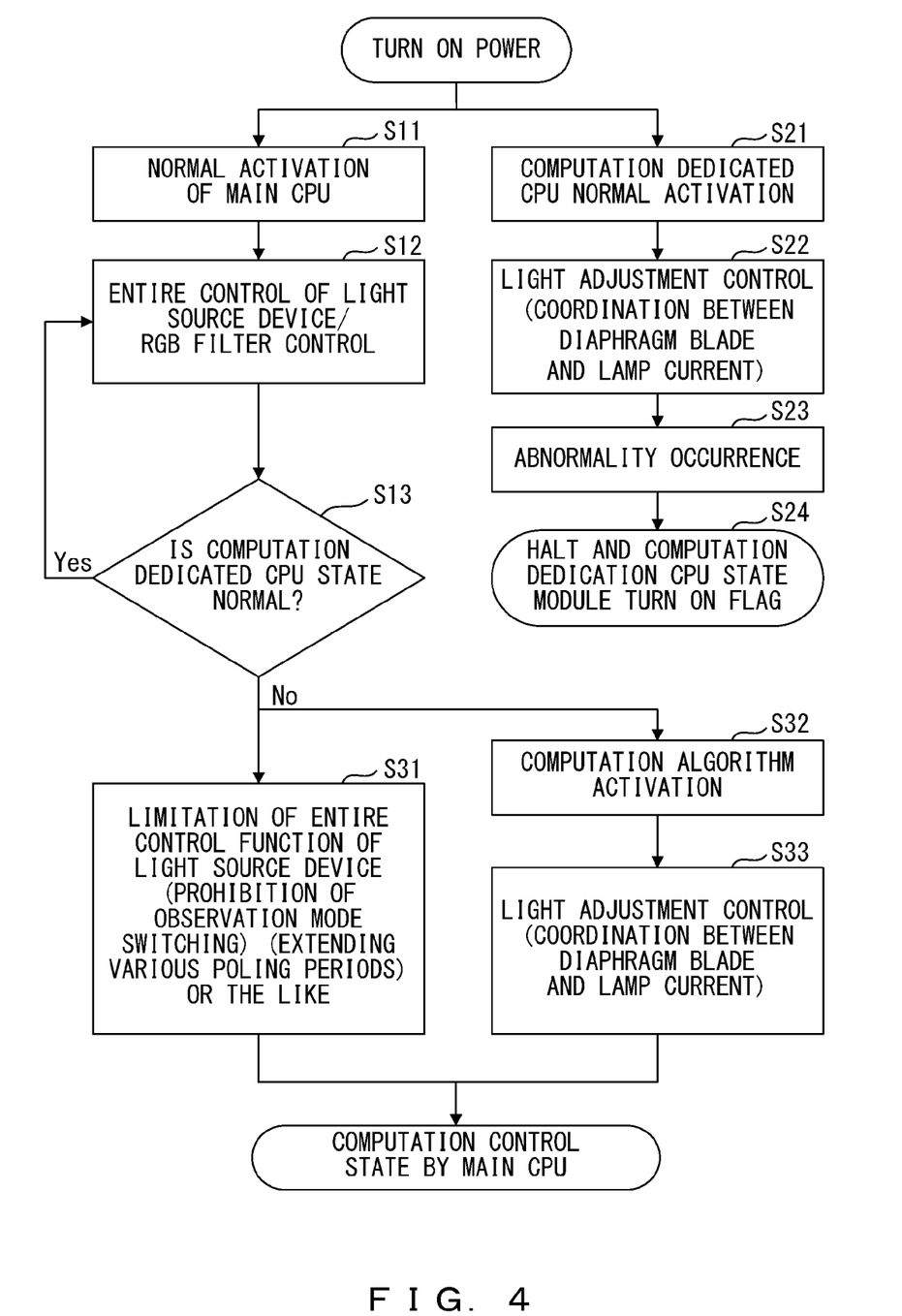
FIG. 4 is a flowchart explaining operations performed by the control device (second)

FIG. 4 shows a specific example of the above second method. In the second method, after a failure has occurred in the computation dedicated CPU 42, the main CPU 41 executes an automatic light adjustment function similar to that executed by the computation dedicated CPU 42, and also simplifies the entire control.

FIG. 4 is a flowchart explaining operations performed by the control device 31 (second). In FIG. 4, steps approximately the same as those in FIG. 3 are denoted by the same symbols, and explanations thereof will be omitted or only given in brief.

As shown in FIG. 4, the processes executed until an abnormality occurs in the computation dedicated CPU 42 are approximately the same as those in FIG. 3.

Specifically, the computation dedicated CPU 42 performs light adjustment control (diaphragm blade control and lamp current control) (step S22) when the system has been activated normally (step S21) by turning on the power. When an abnormality (such as a failure or the like) has occurred (step S23) in the computation dedicated CPU 42 at an arbitrary point in time, the computation dedicated CPU 42 halts, and the computation dedicated CPU state notice module 43 detects this abnormality, and sets the flag (step S24).

When the system has been activated normally (step S11) by turning on the power, the main CPU 41 performs the above various types of entire control (including the RGB filter control in the case of the frame sequential method) (step S12), and periodically checks, for example, whether or not an abnormality has occurred in the computation dedicated CPU 42 (step S13). When an abnormality in the computation dedicated CPU 42 is detected in accordance with the above flag being in an ON state (NO in step S13), the process executes the processes in steps S31, S32, and S33 shown in FIG. 4, even though the process proceeded to steps S14 through S17 in FIG. 3.

Similarly to the case of FIG. 3, it can also be said that the main CPU 41 is in the ordinary mode until the result of step S13 becomes NO, and shifts to the special mode when the result of step S13 has become NO. In other words, the processes by the computation dedicated CPU 42 are the same as that in FIG. 3. While the processes performed by the main CPU 41 in the ordinary mode are the same as those in FIG. 3, the processes in the special mode are different from those in FIG. 3.

In the special mode, the main CPU 41 performs the simplified entire control (step S31). This is implemented by simplifying the function of controlling the entire light source device performed in step S12, and in this simplified control, switching to the observation mode (a mode that uses special light (see Japanese Laid-open Patent Publication No. 2009-142654, etc.)), for example, is prohibited. Also, for example, various poling periods are extended (the main CPU 42 performs the process of periodically referring to various flags such as the flags in the modules 43 and 44 or the flags 46 and 47, and the like, and this cycle (time intervals between references to each flag) is extended). As described above as an example, the entire control is simplified.

In the special mode, the main CPU 41 performs the processes in steps S32 and S33 parallelly to the processes in step S31. Specifically, the main CPU 41 activates a prescribed computation algorithm (step S32) and executes this computation algorithm in order to perform the light adjustment (diaphragm blade control and lamp current control) (step S33).

The process in step S33 may be the same as that in step S22 described above. Note that the computation dedicated CPU 42 also has the prescribed computation algorithm of step S32 above, and the computation dedicated CPU 42 activates this computation algorithm for performing the process in step S21 above in order to perform the process in step S22.

As described above, when an abnormality has occurred in the computation dedicated CPU 42, the main CPU 41 substantially continues the entire light adjustment control (diaphragm blade control and lamp current control) of the computation dedicated CPU 42. However, the main CPU 41 simplifies the entire control of the light source device in order to reduce the processing loads. Note that the processing loads increase compared with the case of the ordinary mode as described above, and the reduction in the processing loads means that increases in processing loads are suppressed.

In the endoscope system according to the present embodiment, both the above main CPU 41 and the computation dedicated CPU 42 can perform the light adjustment (including the simplified light adjustment control). Specifically, the main CPU 41 or the computation dedicated CPU 42 generates a control signal (referred to as a light adjustment signal) for regulating light in accordance with the above photometric signal, and can output the generated control signal to the light-source control circuit 33. Accordingly, as shown in, for example, FIG. 2, a signal line 51 and a signal line 52 are provided for transmitting a light adjustment signal output from the main CPU 41 to the light-source control circuit 33 and a light adjustment signal output from the computation dedicated CPU 42 to the light-source control circuit 33, respectively.

In the ordinary mode, a light adjustment signal is output from the computation dedicated CPU 42 to the light-source control circuit 33, while in the special mode, a light adjustment signal is output from the main CPU 41 to the light-source control circuit 33. However, the light-source control circuit 33 side is not notified of the mode switching between the ordinary mode and the special mode, which requires suitable countermeasures.

As the above countermeasures, various methods can be employed, and two examples thereof will be described herein.

In the first countermeasure, a selector 33a is provided in the light-source control circuit 33, and the signal lines 51 and 52 are connected to the input side of this selector 33a. The selector 33a selects and outputs a signal of either from these signal lines 51 and 52. This is realized by, for example, providing a function (not shown) of detecting a presence or absence of a signal on the two signal lines 51 and 52 so as to make the selector 33a select the signal line "having a signal".

However, when the computation dedicated CPU 42 has failed, there is a possibility that the computation dedicated CPU 42 will not be halted for some reason and will continue to output signals (because the computation dedicated CPU 42 has failed, such signals are meaningless) to the signal line 52, even though the computation dedicated CPU 42 would be halted under normal conditions.

Figure 5:
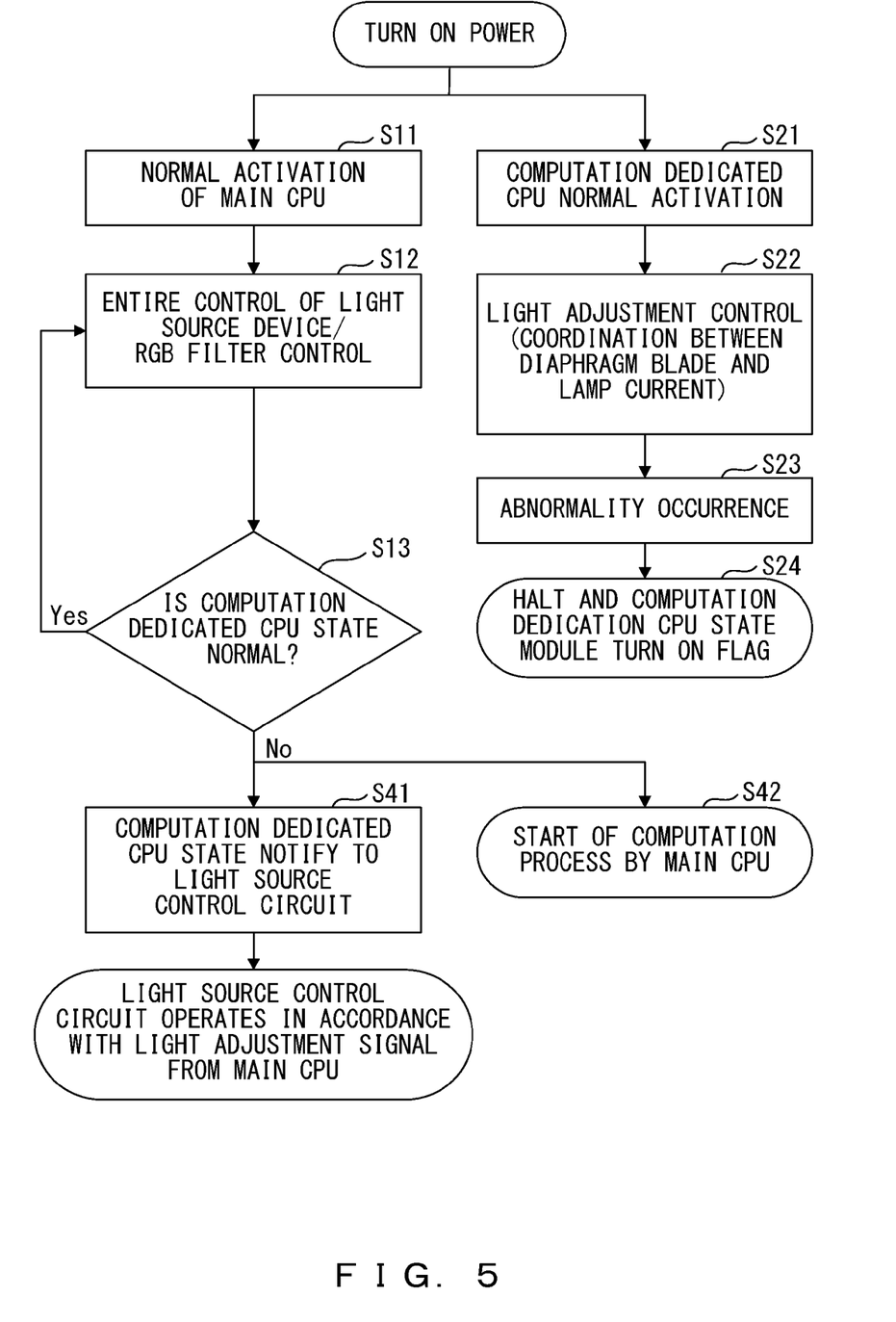
FIG. 5 is a flowchart explaining operations performed by the control device (third)

In response to this situation, in the second countermeasure, the main CPU 41 notify to the light-source control circuit 33 the state of the computation-dedicated CPU as shown in FIG. 2 (and by the processes shown in FIG. 5).

This is explained by referring to FIG. 5.

FIG. 5 is a flowchart (third) explaining operations performed by the control device 31. In FIG. 5, process steps that are approximately the same as those shown in FIG. 3 are denoted by the same symbols, and the explanation thereof will be omitted or given in brief.

As shown in FIG. 5, processes executed before an abnormality occurs in the computation dedicated CPU 42 are approximately the same as those in steps S11 through S13 and S21 through S24 in FIG. 3, and thus are assigned the same step numbers, and the explanations thereof will be omitted.

When an abnormality has occurred in the computation dedicated CPU 42 (NO in step S13), the main CPU 41 notify the state of the computation dedicated CPU 42 (occurrence of abnormality) to the light-source control circuit 33 as shown in FIG. 2 (step S41). The light-source control circuit 33 that has received this notice operates in accordance with a light adjustment signal received from the main CPU 41. For example, the light-source control circuit 33 performs switching control on the selector 33a so as to make the selector 33a select and output light adjustment signals from the main CPU 41. In other words, it is possible to say that while both the first and second countermeasures employ the selector 33a, the light-source control circuit 33 side determines the switching control in the first countermeasure, whereas the switching control is performed in accordance with instructions (notice) from the main CPU 41 in the second countermeasure. As a matter of course, this example is not limiting to the scope of the invention.

In the example shown in FIG. 5, the process for the above special mode by the main CPU 41 is started parallelly to the notice process in step S41 above. This may be executed by using either of the above first and second methods. Specifically, the processes in steps S14 through S17 shown in FIG. 3 may be executed, and the processes in steps S31 through S33 shown in FIG. 4 may also be executed.

In either of the first and the second countermeasures, the selector 33a selects and outputs a light adjustment signal (referred to as a first light adjustment signal) calculated/output by the computation dedicated CPU 42 when the computation dedicated CPU state notice module 43 has determined the computation dedicated CPU 42 to be normal. Also, in either of the first and the second countermeasures, the selector 33a selects and outputs a light adjustment signal (referred to as a second light adjustment signal) calculated/output by the main CPU 41 when the computation dedicated CPU state notice module 43 has determined the computation dedicated CPU 42 to be abnormal.

The light-source control circuit 33, which employs a configuration of actually performing light adjustment in accordance with a light adjustment signal from the CPU, performs light adjustment of the diagnosis light based on the light adjustment signal (either the first light adjustment signal or the second light adjustment signal) which is selected/output by the selector 33a.

When the computation dedicated CPU 42 has failed, light adjustment of the diagnosis light is performed in accordance with the second light adjustment signal. This second light adjustment signal is calculated and output by the main CPU 41 as described above; however, simplified calculations may be performed or calculations approximately the same as those performed by the computation dedicated CPU 42 may be performed (in the latter case, the entire control is simplified). In either case, it is possible for the main CPU 41 to compensate for the light adjustment computation function so as to continue the automatic light adjustment function while suppressing an increase in processing loads on the main CPU 41.

As explained above, in conventional techniques, it has been difficult for the main CPU, which inherently performs various processes for controlling the entire light source device, to execute a light amount adjustment function (light adjustment function) in place of the main CPU when the computation dedicated CPU has failed, because it would make the processing load so heavy. However, according to the endoscope system according to the present embodiment, it is possible to provide an endoscope system, a light source device, etc. that permit a main CPU to perform light adjustment while suppressing an increase in processing loads when a computation dedicated CPU has failed in a light source device provided with a main CPU and a computation dedicated CPU that is exclusively for adjusting the amount of light (light adjustment function) to be emitted to the endoscope. In other words, the main CPU 41 compensates for a light adjustment computation function so as to continue the automatic light adjustment function in order to prevent a situation where the light amount adjustment function (light adjustment function) does not operate, the monitor screens become white/black (they sometimes become white/black completely) so that the image in the cavity becomes difficult to see or becomes almost imperceptible when an abnormality has occurred in the computation dedicated CPU 42. Accordingly, it is possible to prevent the worst situation in which medical procedures (especially the arrest of a hemorrhage) have to be interrupted.

Hereinbelow, explanations will be given also for other features of the endoscope system according to the present embodiment.

First, explanations will be given for features of the program success-failure detection unit 35 in the high-intensity light source device 30 shown in FIG. 1.

In this example, as shown in FIG. 1, the storing region of the non-volatile memory 34 in the high-intensity light source device 30 is divided into a plurality of areas, and accordingly it is also possible to hold the programs respectively of the CPUs 41 and 42 in a duplicated manner. For example, it is possible to store beforehand, in an arbitrary area of the non-volatile memory 34, an arbitrary program (assumed to be a first program in this example) to be executed by the computation dedicated CPU 42, and also to store a second program in a different area. The second program may be the same as the first program, although this example is not limiting to the scope of the present invention.

In a case where the above first program has operating abnormally or in other cases, it is also possible to execute the above second program by, for example, turning on the power again.

Similarly, the main CPU 41 stores, in a duplicated manner in the non-volatile memory 34, an arbitrary program (referred to as the third and fourth programs) to be executed by the main CPU 41. Thereby, when, for example, a third program has operating abnormally, it is also possible to execute the above fourth program by, for example, turning on the power again.

Note that the first and second programs may be completely identical to each other whereas they are stored in different areas, or may be slightly different from each other (for example, one of them may an ordinary program and another of them may a simplified program (only for the above diaphragm blade control or the like)). This substantially applies to the third and fourth programs.

Also, if, for example, the plurality of areas in the non-volatile memory 34 are named area 1, area 2, area 3, and area 4, the first through fourth programs are stored in areas 1 through 4, respectively.

The CPUs 41 and 42 read, from the non-volatile memory 34, the programs that those CPUs themselves implement, and hold the read programs during, for example, the activation of the endoscope system, and they execute those programs thereafter. In this example, it is assumed that the computation dedicated CPU 42 reads the first program from area 1, and the main CPU 41 reads the third program from area 3.

During the above process, the program success-failure detection unit 35 detects whether the reading of the program succeeded or failed. This detection can be performed by a data error detection method used for transmitting and receiving data as a conventional technique, such as for example a CRC (Cyclic Redundancy Check), check sum, or the like used in the field of communications. The program success-failure detection unit 35 uses CRC, check sum or the like in order to check the program read by the CPU 41 or 42 from the non-volatile memory 34, and detects whether or not the program involves an abnormality. When an abnormality is involved in the program, it is determined that the reading of the program failed.

When the program success-failure detection unit 35 has detected a failure in reading of the above program, each of the CPUs 41 and 42 reads the other one of the above duplicated programs. For example, when the program success-failure detection unit 35 has detected a failure in reading of the first program, the computation dedicated CPU 42 reads the second program from area 2. Similarly, when, for example, the program success-failure detection unit 35 has detected a failure in reading of the third program, the main CPU 41 reads the fourth program from area 4. Although the program reading control function as described above is included in the control device 31, it is not necessarily included in the CPU 41 or 42, and may be implemented by a configuration (not shown) included in the control device 31.

Next, explanations will be given for other features of the endoscope system according to the present embodiment by referring to FIGS. 6A through 6C.

The video processor 20 and the high-intensity light source device 30 start coordinated operation through a communication cable connected to the connector 4 and the connector 5 when they are activated. It is desirable to include a configuration to confirm a normal connection of the communication cable because abnormal connection of the communication cable prevents communication.

Figures 6A, 6B:
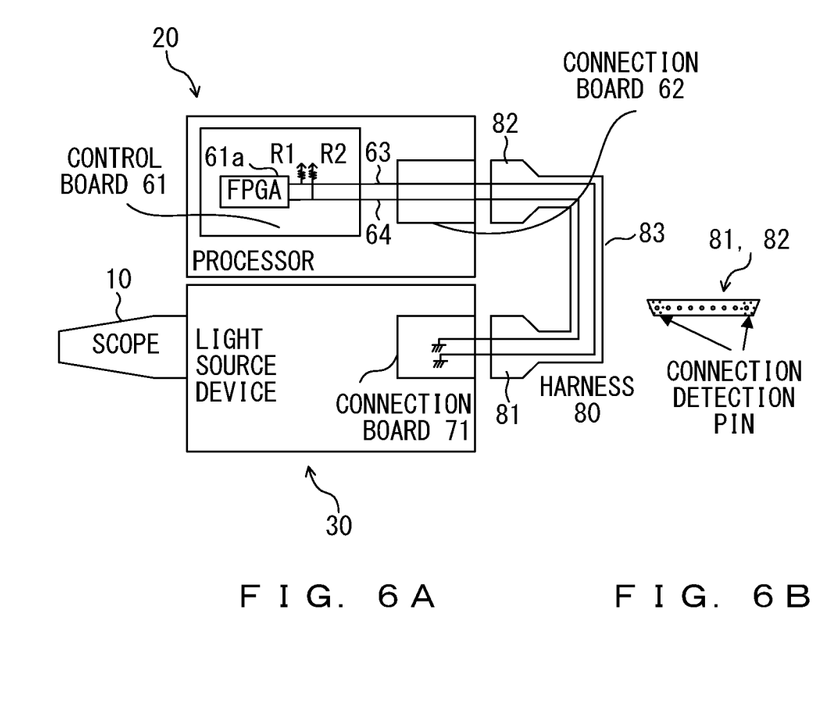
FIGS. 6A 6B, and 6C explain other features (first)

FIG. 6A schematically shows the scope 10, the video processor 20, and the high-intensity light source device 30, and also shows a configuration related to the connection between the video processor 20 and the high-intensity light source device 30 more specifically.

In FIG. 6A, a harness 80 is a communication cable to connect the video processor 20 and the high-intensity light source device 30. In the example shown in FIG. 1, one of the ends of the harness 80 is connected to the connector 4 of the video processor 20, and the other end is connected to the connector 5 of the high-intensity light source device 30. A connection board 62 in FIG. 6A corresponds to the connector 4, and a connection board 71 in FIG. 6A corresponds to the connector 5. A control board 61 corresponds to the control device 21.

The harness 80 includes a cable portion 83, and connector portions 81 and 82 at the ends of the cable portion 83 in FIG. 6A. The connector portion 81 is connected to the connection board 71 whereas the connector portion 82 is connected to the connector board 62.

In this example, both of the connector portions 82 and 81 include connection detection pins at their ends. In FIG. 6A, shows lines corresponding to these connection detection pins, and lines for other pins (the example shown in FIG. 6B includes seven more pins) are omitted, and the explanations thereof will also be omitted.

As shown in FIG. 6A, in the connection board 71 (connector 5) of the high-intensity light source device 30, the portions to be connected with the above two connection detection pins of the connector portion 81 are grounded. Wiring patterns 63 and 64 are connected to the portions to be connected with the two connection detection pins of the connector portion 82 in the connector board 62 (connector 4) of the video processor 20. These wiring patterns 63 and 64 are connected with a power source (not shown) via resistors R1 and R2 on the control board 61.

In the above described configuration, it is possible for an FPGA 61a on the control board 61 to detect a presence or absence of the connection of the harness 80 (whether or not the connection between the video processor 20 and the high-intensity light source device 30 is normal) by monitoring the voltage or the like in the wiring patterns 63 and 64.

Configurations for detecting the presence or absence as described above are conventional techniques. However, the present method employs a configuration having two connection detection pins; one connection detection pin for each of the ends of a connector. Such a configuration has communication cables connected to the connectors 4 and 5 of the video processor 20 and the high-intensity light source device 30; however, when the connection is not complete so that not all pins are connected in one or both of the connectors 4 and 5 (incomplete connection (for example a condition in which the connector is inserted incompletely)), the present invention presents remarkable effects.

In other words, when there is only one connection detection pin and that connection detection pin is connected, an abnormality cannot be detected even when the connection is incomplete and not all pins are connected. Also, even when there are two connection detection pins, if those two pins are provided, for example, at one of the ends of a connector, the other end of the connector can sometimes be connected incompletely even when the two pins are connected.

By contrast, when a configuration having one connection detection pin at each of the ends of a connector is employed as shown in FIG. 6B, if two connection detection pins are connected, all the other pins are also connected completely, making it possible to detect a presence or absence of the connection safely.

Also, this configuration can be applied to connections between boards.

Figure 6C:
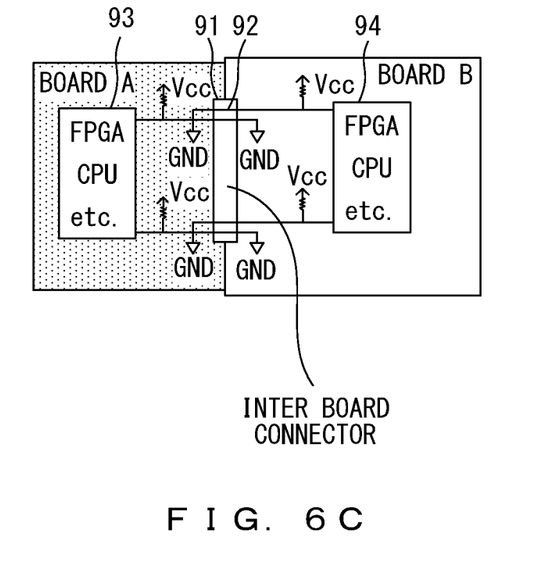

Specifically, as shown in, for example, FIG. 6C, as a conventional technique, two boards A and B are connected to each other using inter board connectors 91 and 92 that are provided to boards A and B, respectively. Also, the present methods can securely detect whether or not the connection between the inter board connectors 91 and 92 is normal. Further, FIG. 6C shows a situation in which the inter board connectors 91 and 92 have already been connected, and the inter board connector 91 is provided to board A, and the inter board connector 92 is provided to board B.

As an example, it is possible for the configurations of the control device 21 and the control device 31 to employ the configuration shown in FIG. 6C. For example, when the control device 31 employs the configuration in FIG. 6C, it is also possible to say that the FPGA (CPU) 93 on board A corresponds to the main CPU 41, and the FPGA (CPU) 94 on board B corresponds to the computation dedicated CPU 42.

The example shown in FIG. 6C employs a configuration in which four connection detection pins are provided, i.e., two connection detection pins are provided to each of the ends of each of the inter board connectors 91 and 92. The configuration of the four pins is approximately the same as those shown in FIG. 6A and FIG. 6B. In this configuration, one of boards A and B is grounded and the other is connected to the power source for each pin, as shown in FIG. 6C.

When it is assumed that the number of pins of each of the inter board connectors 91 and 92 is M and those pins are named pin (1) through pins (M), pins (1), pins (2), pins (M−1), and pins (M) are connection detection pins. For example, pin (1) of the inter board connector 91 and pin (1) of the inter board connector 92 are connected (this applies to the other pins, and pins having the same numbers are connected to each other).

It is assumed that the pins depicted at the highest position (position on drawing) of the inter board connectors 91 and 92 in FIG. 6C are pins (1), and the pins depicted at the lowest position (position on drawing) are pins (M). Thereby, as shown in FIG. 6, for example, pin (1) of the inter board connector 91 is connected to GND, and pin (1) of the inter board connector 92 is connected to the FPGA (CPU) 94 on board B and is also connected to a power source Vcc. Thereby, the FPGA (CPU) 94 can detect whether or not pins (1) are connected. Similarly, as shown in FIG. 6C, pin (M−1) of the inter board connector 91, for example, is connected to GND, and pin (M−1) of the inter board connector 92 is connected to Vcc and the FPGA (CPU) 94 on board B. Thereby, the FPGA (CPU) 94 can detect whether or not pins (M−1) are connected.

On the basis of the above, the FPGA (CPU) 94 determines that the inter board connector 91 and the inter board connector 92 have been connected normally when the FPGA (CPU) 94 has detected that both of pins (1) and pins (M−1) are connected.

This applies to the FPGA (CPU) 94 on board A so that the FPGA (CPU) 94 on board A determines that the inter board connector 91 and the inter board connector 92 have been connected normally when the FPGA (CPU) 94 on board A has detected that both of pins (2) and pins (M) are connected.

Although a configuration in which two connection detection pins are provided to each of the ends (four pins in total) is shown, this example is not limiting to the scope of the present invention, and a configuration in which a connection detection pin may be provided to each of the ends (two pins in total) may be employed. In such a case, one of the FPGAs (CPUs) 93 and 94 detects whether or not the inter board connector 91 and the inter board connector 92 are connected normally.

In the above example, it cannot be said that pins (2) and pins (M−1) are strictly at both ends. However, it can be said that they are approximately at both ends, and cause almost the same effects, and accordingly these pins (2) and (M−1) are also defined as pins at both ends.

In addition, when an unconnected state or incomplete insertion is detected, such a situation is reported by using a buzzer, a monitor device, or the like and the control is limited (for example, the light amount is minimized). As for the reporting, for example, the control device 21 sounds a buzzer 24 or displays an error message or the like on a monitor 6 in the case of a video processor 20. In the case of the high-intensity light source device 30, the control device 31 sounds a buzzer 36.

As described above, by using the connection detection method shown in FIGS. 6A and 6B, it is possible to detect connection even for inter board connection within a device as shown in FIG. 6C by using a process similar to that used for inter board connection.

Also, when the video processor 20 and the high-intensity light source device 30 are turned ON, the control devices 21 and 31 read setting values from the non-volatile memory 23 and non-volatile memory 24 so as to start activation processes (this is a conventional operation, and explanations will not be given for setting values or activation processes).

Also, it has been conventional practice to, for example, display an arbitrary comment on the endoscope screen on the monitor 6.

In the present method, users are prompted beforehand to input an arbitrary comment by using the input device 7 (such as a keyboard or the like) and the input comment is stored in the non-volatile memory 23. The control device 21 reads this comment from the non-volatile memory 23 in addition to the above setting values in the activation processes. The control device 21 displays the read comment on the endoscope screen (the comment displaying field on the screen) of the monitor 6.

As described above, it is also possible to activate the system by displaying a comment/initial value.

Also, when, for example, shielded twisted-pair cables without a drain wire are used as a cable connected to the connectors 1 through 5 shown in FIG. 5, a heat-shrinkable tube that is independent from a shield processed part may be used so as to make the pair cables and the electric wire (ground wire 107) closely contact each other to enhance EMI performance. This feature will be explained by referring to an example shown in FIGS. 7A through 7C.

Figure 7A:
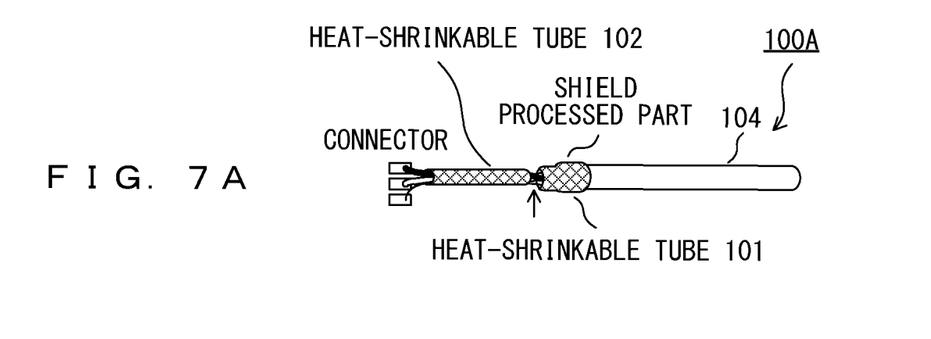
FIGS. 7A 7B, and 7C explain other features (second).
Figure 7B:
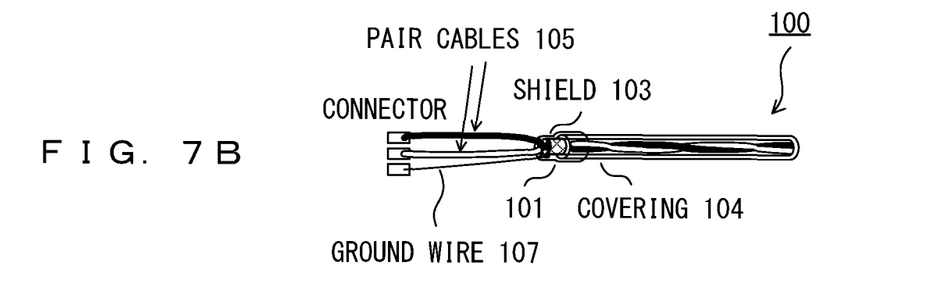
Figure 7C:
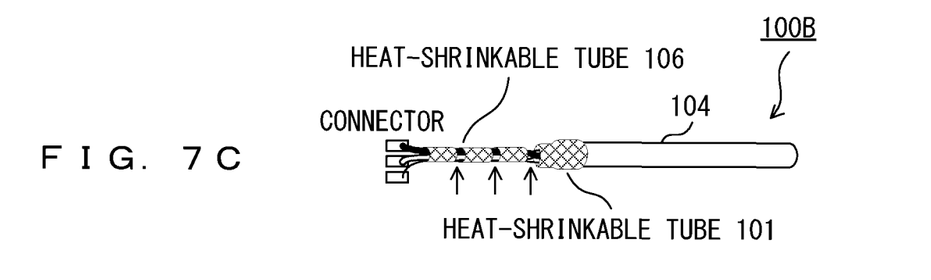

FIGS. 7A through 7C show a cable 100 having pair cables 105 coated with a shield 103 and a covering 104. Connectors to be connected to the connectors 1 through 5 or the like have to be provided to both ends of the cable 100, and the pair cables 105, the ground wire 107, and the like have to be connected (by soldering, etc.) to this connector. The ground wire 107 is an electric wire connected to the shield 103.

As part of the above operations, the tip portions of the shield 103 and the covering 104 are removed as shown in FIG. 7B, and part of the thus exposed shield 103 is coated with a heat-shrinkable tube 101 (the above "shield processed part" refers to this part). This is the same as a conventional technique. In other words, the cable 100 shown in FIG. 7B can be interpreted as a conventional configuration. In FIG. 7B, the inside of the covering 104 and the heat-shrinkable tube 101 are shown in a perspective manner.

In this method, in addition to the above configuration, a cable 100A or a cable 100B shown in FIG. 7A or 7C is configured. In other words, the pair cables 105 and the ground wire 107 exposed by removing the shield 103 and the covering 104 are coated with a heat-shrinkable tube (a heat-shrinkable tube 102 or a heat-shrinkable tube 106 in the figure) that is different from the heat-shrinkable tube 101 of the "shield processed part".

As a matter of course, heat-shrinkable tubes (101, 102, and 106) shrink when heat is applied to them, and FIGS. 7A and 7C show a state after applying heat to these heat-shrinkable tubes. By shrinking the heat-shrinkable tubes 102 and 106 as described above, the heat-shrinkable tubes 102 and 106 closely contact the pair cables 105 or the like as shown in FIG. 7 so as to coat the pair cables 105 or the like so that the pair cables and electric wires (ground wires) closely contact each other, leading to improvement in the EMI performance.

FIGS. 7A and 7C are different in that the heat-shrinkable tube 102 in FIG. 7A is a single tube that is relatively long, while the heat-shrinkable tubes 106 in FIG. 7C are plural (three in the example) tubes.

As described above, according to the present feature, it is possible to use an innovative manner in the processing of heat-shrinkable tubes, and to secure the performance of EMI while securing the flexibility and the workability.

According to the endoscope system, the light source device, and the like of the present invention, the main CPU can perform light adjustment while suppressing an increase in the processing loads when the computation dedicated CPU has failed in a light source device that has a computation dedicated CPU exclusively for adjusting the amount of light to be supplied to the endoscope (light adjustment) and a main CPU. Thereby, particularly when a computation dedicated CPU has failed in under some medical examination, it is possible to avoid a situation that prevents the continuation of the medical examination.

What is claimed is:

1. An endoscope system that includes an endoscope for emitting illumination light with which a subject is irradiated, comprising:

an illumination unit for emitting illumination light with which a subject is irradiated;

an image pickup unit that is provided to the endoscope and that is for picking up an image of the subject illuminated by illumination light;

a photometric signal generation unit for generating a photometric signal from the image pickup unit;

a first computation unit for computing/outputting a first light adjustment signal in accordance with the photometric signal generation unit;

a computation unit state detection unit for detecting a state of the first computation unit;

a second computation unit for executing partial control of the endoscope system, that is provided as a computation unit different from the first computation unit, and that computes/outputs a second light adjustment signal in accordance with the photometric signal generation unit together with executing the partial control while suppressing an increase in a processing load when the computation unit state detection unit has determined the first computation unit to be abnormal;

a light adjustment signal control unit for outputting the first light adjustment signal computed/output by the first computation unit when the computation unit state detection unit has determined the first computation unit to be normal, and for outputting the second light adjustment signal computed/output by the second computation unit when the computation unit state detection unit has determined the first computation unit to be abnormal; and
a light adjustment unit for regulating the illumination light in accordance with the light adjustment signal output from the light adjustment signal control unit.

2. The endoscope system according to claim 1, wherein:
the second computation unit reduces processing load of the partial control or performs computation of the second light adjustment signal whose processing load has been reduced as compared with the first computation, when the computation unit state detection unit has determined the first computation unit to be abnormal.

3. The endoscope system according to claim 1, wherein:
the second computation unit performs diaphragm blade control, but does not perform lamp current value control for computation/output of the second light adjustment signal when the computation unit state detection unit has determined the first computation unit to be abnormal.

4. The endoscope system according to claim 1, wherein:
the second computation unit computes/outputs, when the computation unit state detection unit has determined the first computation unit to be abnormal, the second light adjustment signal based on the photometric signal generation unit in a cycle longer than a cycle for the first computation unit to perform computation when the computation unit state detection unit has determined the first computation unit to be normal.

5. The endoscope system according to claim 1, wherein:
the second computation unit outputs, when the computation unit state detection unit has determined the first computation unit to be abnormal, the second light adjustment signal based on the photometric signal generation unit in a range narrower than an output range of the first computation unit when the computation unit state detection unit has determined the first computation unit to be normal.

6. The endoscope system according to claim 1, wherein:
the second computation unit starts computation/output of the second light adjustment signal based on the photometric signal generation unit and also switches control from entire control of the endoscope system to a simplified entire control when the computation unit state detection unit has determined the first computation unit to be abnormal, 7. The endoscope system according to claim 1, further comprising:
a first storing unit for storing a computation program executed by the first computation unit;
a second storing unit for storing another computation program executed by the first computation unit;
a computation program reading success-failure detection unit for detecting a success/failure in reading of the computation program from the first storing unit when the endoscope system is activated; and
a computation program reading control unit for reading the another computation program from the second storing unit, and setting the another computation program in the computation unit when the computation program reading success-failure detection unit has detected a failure in reading of the computation program.

8. A light source device in an endoscope system including an endoscope that emits illumination light with which a subject is irradiated and that picks up an image of a subject illuminated by the illumination light so as to output a pickup image signal, a video processor that also has a function of generating a photometric signal in accordance with the pickup image signal, and a light source device that inputs the photometric signal so as to supply to the endoscope the illumination light adjusted in accordance with the photometric signal, comprising:
a first computation unit for computing/outputting a first light adjustment signal in accordance with the photometric signal;
a computation unit state detection unit for detecting a state of the first computation unit;
a second computation unit that is for performing entire control of the light source device, that is different computation unit from the first computation unit, and that computes/outputs a second light adjustment signal based on the photometric signal together with executing the entire control while suppressing an increase in a processing load when the computation unit state detection unit has determined the first computation unit to be abnormal;
a light adjustment signal control unit for outputting the first light adjustment signal computed/output by the first computation unit when the computation unit state detection unit has determined the first computation unit to be normal, and for outputting the second light adjustment signal computed/output by the second computation unit based on the photometric signal when the computation unit state detection unit has determined the first computation unit to be abnormal; and
a light adjustment unit for regulating the illumination light in accordance with the light adjustment signal output from the light adjustment signal control unit.

* * * * *